United States Patent [19]

Aoyagi

[11] Patent Number: 4,477,459
[45] Date of Patent: Oct. 16, 1984

[54] FUNGICIDAL 4-SUBSTITUTED-5-TRIFLUOROMETHYL-3-(1,2-DICHLORO-2-CYANOVINYL THIO)-1,2,4-TRIAZOLES

[75] Inventor: Edward I. Aoyagi, Petaluma, Calif.

[73] Assignee: Chevron Research Company, San Francisco, Calif.

[21] Appl. No.: 518,340

[22] Filed: Jul. 29, 1983

[51] Int. Cl.³ .................... A01N 43/64; C07D 249/12
[52] U.S. Cl. .................................... 424/269; 548/263; 564/18; 260/465.2; 260/465 G
[58] Field of Search ......................... 548/262; 424/269

[56] References Cited

U.S. PATENT DOCUMENTS

| | | | |
|---|---|---|---|
| 4,097,599 | 6/1978 | Evans et al. | 548/262 |
| 4,238,405 | 12/1980 | Felix | 260/239 BF |
| 4,269,988 | 5/1981 | Felix | 548/263 |
| 4,414,221 | 11/1983 | Parsons et al. | 548/263 |

FOREIGN PATENT DOCUMENTS 681376 10/1952 United Kingdom ............... 548/263

Primary Examiner—Alton D. Rollins
Attorney, Agent, or Firm—S. R. LaPaglia; T. G. DeJonghe; S. L. Biggs

[57] ABSTRACT

Compounds of the formula:

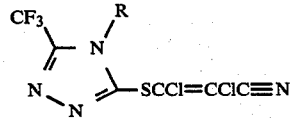

wherein R is lower alkyl or lower alkenyl are fungicidal.

12 Claims, No Drawings

4,477,459

FUNGICIDAL 4-SUBSTITUTED-5-TRIFLUOROMETHYL-3-(1,2-DICHLORO-2-CYANOVINYL THIO)-1,2,4-TRIAZOLES

BACKGROUND OF THE INVENTION

The present invention relates to novel triazole fungicides.

With the world more dependent for food on an ever decreasing amount of cultivated farmland, it is increasingly important to develop effective fungicides which protect crops and their seeds from fungal destruction.

U.S. Pat. No. 4,308,050 discloses biocidal compounds of the formula $$R'-C\underset{\underset{R}{N}}{\overset{N-N}{\diagup}}CSC=CC\equiv N$$
                    Cl Cl wherein R and R' are independently selected from the group consisting of $C_1$-$C_4$ alkyl including methyl, ethyl, propyl and butyl, $C_2$-$C_4$ alkenyl including ethenyl, propenyl and butenyl, phenyl, and substituted phenyl wherein the substituents are selected from the group consisting of $NO_2$, $CH_3$, Cl and Br.

U.S. Pat. No. 4,238,405 discloses fungicidal compounds of the formula:

$$R-S(O)_n-\underset{Cl}{\overset{Cl}{C}}=\underset{}{\overset{}{C}}-C\equiv N$$

wherein n is 0, 1, or 2 and R is selected from the group consisting of alkyl, alkylcarbalkoxy, cyclohexyl, halophenyl, benzyl, N,N-di-lower alkyl carbamoyl, hexamethyleneimino carbonyl, pyrimidyl, lower alkyl substituted imidazole, benzothiazole and O,O-di-lower alkyl thiophosphoryl; with the proviso that when n is O, R is other than alkyl or cyclohexyl.

SUMMARY OF THE INVENTION

The present invention relates to fungicidal triazole compounds of the formula:

$$\underset{N\diagdown_{N}}{\overset{CF_3}{\diagup}}\underset{}{\overset{R}{\diagdown}}SCCl=CClC\equiv N \qquad I$$

wherein R is lower alkyl or lower alkenyl.

Among other factors, the present invention is based upon my surprising finding that the compounds of this invention are effective as fungicides. In particular, these compounds are especially effective in combatting certain plant fungal diseases. In addition, some of these compounds are especially active in the control of seed fungus, and may be used to treat many types of grain seeds to protect them from fungus attack, both during storage and after planting.

Preferred are compounds where R is alkyl of up to 3 carbon atoms or allyl.

Especially preferred R groups include methyl.

Definitions

As used herein, the following terms have the following meanings, unless expressly stated to the contrary.

The term "alkyl" refers to both straight- and branced-chain alkyl groups. The term "lower alkyl" refers to both straight- and branced-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group $-(CH_2)_m-$ wherein m is an integer greater than zero. Typical alkylene groups include methylene, ethylene, propylene and the like.

The term "alkenyl" refers to unsaturated alkyl groups having a double bond [e.g., $CH_3CH=CH(CH_2)_2$] and includes both straight- and branced-chain alkenyl groups. "Lower alkenyl" refers to groups having a total of from 3 to 6 carbon atoms. Typical lower alkenyl groups include, for example, propenyl, but-3-enyl, hex-4-enyl, 2-methyl-pent-4-enyl, and the like.

The term "halo" or "halogen" refers to the groups fluoro, chloro, bromo and iodo.

The term "1,2,4-triazole" refers to the group $$\underset{N\diagdown_{N}}{\overset{N}{\diagup}}\diagdown$$

which has the conventional numbering scheme as follows:

$$\underset{N\underset{}{\overset{1}{\diagdown}}_{N}^{2}}{\overset{5\overset{N}{\diagup}^{4}}{\diagup}}\overset{3}{\diagdown}$$

DETAILED DESCRIPTION OF THE INVENTION

The compounds to the present invention may be prepared according to the following reaction scheme:

$$R-NCS + H_2NNH_2 \longrightarrow R-NH\overset{\overset{S}{\|}}{C}NHNH_2 \qquad (1)$$
$$\text{II} \qquad \text{III} \qquad \qquad \text{IV}$$

$$IV + CF_3C\overset{\overset{O}{\diagup}}{\diagdown_{OH}} \longrightarrow \underset{N\diagdown_{N}}{\overset{CF_3}{\diagup}}\underset{}{\overset{R}{\diagdown}}SH \qquad (2)$$
$$\text{V} \qquad\qquad\qquad \text{VI}$$

$$\underset{Cl}{\overset{Cl}{\diagdown}}C=C\overset{Cl}{\diagdown}_{Cl}-C\overset{\overset{O}{\|}}{\diagdown_{Cl}} + NH_4OH \longrightarrow \underset{Cl}{\overset{Cl}{\diagdown}}C=C\overset{Cl}{\diagdown}-\overset{\overset{O}{\|}}{C}NH_2 \qquad (3)$$
$$\text{VII} \qquad \text{VIII} \qquad\qquad \text{IX}$$

$$IX + Rg \longrightarrow \underset{Cl}{\overset{Cl}{\diagdown}}C=\overset{Cl}{\overset{|}{C}}-C\equiv N \qquad (4)$$
$$\text{X} \qquad\qquad \text{XI}$$

-continued $$VI + XI + b \xrightarrow{} I \quad (5)$$

wherein R is as previously defined in connection with Formula I, b is a base and Rg is a dehydration reagent.

Reaction (1) is conducted by combining approximately equimolar amounts of II and III in solvent. Although the reactants may be added in any order, it is preferred to add III in a small amount of solvent to II in solvent. Suitable solvents include inert organic solvents such as ethyl ether, methylene chloride, dimethoxy ethane, and the like. The reaction is conducted at a temperature of about 0° C. to about 40° C. or, for convenience, at ambient temperature. The reaction is generally complete within about one to about 24 hours. The product IV may be isolated by conventional procedures such as filtration, recrystallization, and the like.

Reaction (2) is conducted by combining IV and V. It is preferred to use an excess of V, which then also serves as a solvent. The reaction is conducted at a temperature of about 25° C. to about 75° C., preferably at reflux. The reaction is generally complete within about one-half to about 24 hours. The product, VI, is isolated by conventional procedures such as extraction, filtration, stripping, recrystallization, and the like.

Reaction (3) is conducted by combining VII and an excess of VIII. It is preferred to add VII to cooled (about 0 to about 5° C.) concentrated (28%) VIII. The reaction is conducted at a temperature of about −10° C. to about 30° C., and is generally complete within about ½ to about 24 hours. A solution of ammonia gas in a solvent such as diethyl ether or methylene chloride may be substituted for VIII. The product IX is isolated by conventional procedures such as filtration, recrystallization, and the like.

Reaction (4) is conducted by combining IX and X in solvent. Suitable dehydration reagents include thionyl chloride, a combination of phosphorus oxychloride and ammonium chloride, as well as other similar reagents suitable for dehydrating an amide to yield the corresponding nitrile well known to those skilled in the art. Suitable solvents include inert organic solvents such as chloroform, methylene chloride, and the like. The reaction is conducted at a temperature of about 25° C. to about 100° C., preferably from about 40° C. to about 62° C., and is generally complete within about 3 to about 24 hours. The product, XI, is isolated by conventional procedures such as filtration, stripping, distillation, chromatography, and the like.

Reaction (5) is conducted by combining approximately equimolar amounts of VI, XI and XII in solvent. Suitable bases, XII, include organic and inorganic bases such as triethylamine, pyridine, potassium carbonate, sodium carbonate, and the like. The reaction is conducted at a temperature of about 20° C. to about 100° C., preferably from about 20° C. to about 50° C. or, for convenience, at ambient temperature. The reaction is generally complete within about 1 to about 72 hours. Suitable solvents include inert organic solvents such as methylene chloride, dimethoxy ethane, and the like. The product I is isolated by conventional procedures such as washing, drying, stripping, crystallization, chromatography, and the like.

Utility

The compounds of the invention are effective in controlling fungal infections.

Some of the compounds of this invention are particularly effective in protecting seed from soil borne fungi such as *Rhizoctonia solari, Pythium ultimum, Fusarium monilofroma,* and the like.

The compounds of this invention are particularly effective in controlling plant fungal infections caused by organisms such as *plasmopara viticola.* Some of the compounds of this invention are also useful for controlling leaf blights caused by organisms such as *Phytophthora infestans conidia, Alternaria solani conidia,* and *Septoria apii.* Some of the compounds of this invention are also useful for controlling fungal infections caused by *Uromyces phaseoli tipica, Erysiphe polygoni,* and *Piricularia oryzae.* However, some fungicidal compounds of this invention may be more fungicidally active than others against particular fungi.

When used as a seed treater, the seeds are coated with a fomulation of the compound by tumbling or other conventional methods. Generally, the seeds are treated with compound at a rate of about 0.4 to about 2.5 ounces compound per hundredweight seed.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkyl-aryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated napthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of 4-Allylthiosemicarbazide

To a stirred mixture of 8.1 g [8 ml (0.252 moles)] hydrazine and ethyl ether, 25 g [24.7 ml (0.252 mole)], allyl isothiocyanate in a small amount ethyl ether were added dropwise. The product began to precipitate immediately. After the addition was completed, the reaction mixture was stirred an hour and then allowed to sit overnight. The mixture was then filtered to give 29.0 g of the above-identified product as a light orange solid.

EXAMPLE 2

Preparation of 4-Allyl-5-trifluoromethyl-3-mercapto-1,2,4-triazole

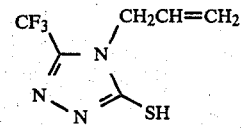

To 50 g (0.38 mole) 4-allylthiosemicarbazide in a round bottom flask, 97.5 g [65 ml (0.85 mole)] trifluoroacetic acid were added. The reaction mixture was refluxed for one-half hour. The reaction mixture was cooled, diluted with ether and dried over magnesium sulfate. The mixture was stripped and the residue placed on filter paper to dry, yielding 17.3 g of the product as a solid, melting point 111° C.

Elemental analysis for sulfur showed: calculated % 15.33; found % 16.4.

EXAMPLE 3

Preparation of Trichloroacrylonitrile

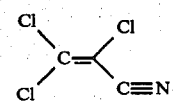

(a) To 25 g (0.129 mole) trichloroacryloyl chloride which were stirred and cooled to 0° C., 100 ml concentrated (28%) ammonium hydroxide were added dropwise. A white solid formed. The reaction mixture was filtered and the precipitate was washed with water. The precipitate was air-dried ovenight to yield 19.2 g, of the amide which was used in step (b) without further purification.

(b) A mixture of 19.2 g (0.110 mole) of the product of step (a) and 26 g (0.22 mole) thionyl chloride in 200 ml chloroform was refluxed about 3 days. The reaction mixture was washed with water and then cooled on dry ice, yielding a crystalline product. The mixture was filtered; the filtrate was stipped to give an oil which later crystallized yielding a mushy solid. The crude product was chromatographed on silica gel, eluting with methylene chloride. The high Rf component was isolated and was stripped to give 3.3 g of the product, as an oil.

EXAMPLE 3A

Preparation of Trichloroacrylonitrile

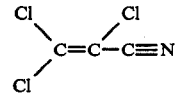

(a) To 300 ml concentrated (28%) ammonium hydroxide cooled to 0° C., 100 g [61 ml (0.51 mole)] trichloroacryloyl chloride were added dropwise with stirring, maintaining the temperature of the reaction mixture at about 0 to about 5° C. The product precipitated immediately. The reaction mixture was stirred for a few minutes after the addition was complete and then filtered. The precipitate was dried in a vacuum oven (melting during drying at about 110° C.), yielding 78.5 g. The product was used in step (b) without further purification.

(b) A mixture of 78.5 g (0.45 mole) of the product of step (a), 40.4 g [24.6 ml (0.26 mole)] phosphorusoxy chloride, and 50 g ammonium chloride in 300 chloroform was heated at reflux for about 24 hours over several days. The mixture was filtered. The filtrate was partially stripped and then distilled at reduced pressure. The cut isolated at boiling point about 55° C. to about 57° C. at 40 mm Hg, yielded 32.0 g of the above- identified product.

EXAMPLE 4

Preparation of 4-Allyl-5-trifluoromethyl-3-(1,2-dichloro-2-cyanovinyl thio)-1,2,4-triazole

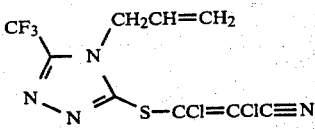

A mixture of 4.0 g (0.019 mole) 4-allyl-5-trifluoromethyl-3-mercapto-1,2,4-triazole (the product of Example 2), 3.0 g (0.019 mole) trichloroacrylonitrile (the product of Example 3A), and 2.65 ml (0.019 mole) triethylamine in 100 ml methylene chloride was stirred at room temperature for several days. The reaction mixture washed with water, dried over magnesium sulfate, and stripped to give a yellow oil. Further purification by chromatography gave 3.6 g of the product as an oil which later crystallized, melting point 45°–48° C.

Elemental analysis for $C_9H_5Cl_2F_3N_4S$ showed: Calculated % C32.84, %H 1.53, and %N 17.02; found % 32.93, %H 1.57, and %N 17.22.

EXAMPLE 5

Preparation of 4-Methylthiosemicarbazide

To a rapidly stirred mixture of 66 g of 97% (2.0 mole) hydrazine in 1,000 ml ether, 146 g (2.0 mole) methylisothiocyanate in 100 ml ether was added. During the addition the reaction mixture was occasionally cooled with a dry-ice acetone bath to keep the reaction mixture at a gentle reflux. Towards the midway of the addition, a pale yellow solid formed. After the addition was complete, the reaction mixture was stirred vigorously at room temperature for one hour. The solids were filtered, washed with ether and air-dried to give approximately 200 g of the product as a yellow solid.

EXAMPLE 6

Preparation of 3-mercapto-4-methyl-5-trifluoromethyl-1,2,4-triazole

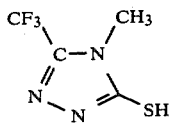

In a 500-ml flask, 100 g (0.95 mole) 4-methylthiosemicarbazide and 155 g [100 ml (1.36 mole)] trifluoroacetic acid were combined, refluxed 3 hours, and then allowed to stand overnight. Since the reaction mixture solidified overnight, it was heated to solution and then added to ice. The precipitated solid was filtered, washed with water and air-dried. The solid was dissolved in hot benzene and the water was separated. The benzene solution was concentrated cooled, and filtered to give the product as crystals.

EXAMPLE 7

Preparation of 4-Methyl-5-trifluoromethyl-3-(1,2-dichloro-2-cyanovinyl thio)-1,2,4-triazole

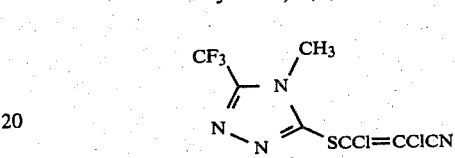

To a stirred mixture of 3.5 g (0.0192 mole) 3-mercapto-4-methyl-5-trifluoromethyl-1,2,4-triazole (the product of Example 6) and 3.0 g (0.0192 mole) trichloroacrylonitrile in methylene chloride, 1.94 g (0.0192 mole) triethylamine in methylene chloride were added dropwise. The reaction mixture was stirred at room temperature for several days. The reaction mixture was washed with water and then dried over magnesium sulfate. The organic phase was passed through a short silica gel ($SiO_2$) column and stripped to give a thick oil which soon crystallized. The material was recrystallized from methylene chloride/hexane to give 1.5 g of the above-identified product as a light yellow solid, melting point 90°–94° C.

Elemental analysis for $C_7H_3Cl_2F_3N_4S$ showed: calculated %C 27.73, %H 1.00, and %N 18.48; found %C 29.97, %H 1.26 and %N 21.

Compounds made in accordance with Examples 1 to 7 are shown in Table I.

In addition, by following the procedures described herein and in Examples 1 to 7, using the appropriate starting materials, the following compounds are made:

4-n-propyl-5-trifluoromethyl-3-(1,2,-dichloro-2-cyanovinyl thio)-1,2,4-triazole;

4-isopropyl-5-trifluoromethyl-3-(1,2dichloro-2-cyanovinyl thio)-1,2,4-triazole; and 4-(2-methylallyl)-5-trifluoromethyl-3-(1,2-dichloro-2-cyanovinyl thio)-1,2,4-triazole.

EXAMPLE A

Mycelial Inhibition

The compound was evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium monilofroma, Botrytis cinerea* and *Aspargillos niger*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99% control of the fungus (ED$_{99}$). The effectiveness of the compound for fungicidal activity is reported in Table II in terms of the percent of the ED$_{99}$ of the test compound of the ED$_{99}$ of the standard Difolatan ®.

EXAMPLE B

Bean Powdery Mildew

The compound was tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

EXAMPLE C

Tomato Late Blight

The compound was tested for the preventative control of the Tomato Late Blight oganism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE D

Celery Late Blight

The Celery Late Blight test was conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

EXAMPLE E

Tomato Early Blight

The compound was tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a non-ionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

EXAMPLE F

Grape Downy Mildew

The compound was tested for the control of the Grape Downy Mildew organism, *Plasmopara viticola*. Seedlings of *Vitis vinifera* var. Emperor (7+ weeks old) were used as hosts. The plants were sprayed with a 250 ppm solution of the test compound in an acetone and water solution containing a small amount of non-ionic emulsifier. The treated plants were inoculated one day later by spraying them with a spore suspension of the organsism. The treated plants were then held in a greenhouse at a temperature of about 68° F. to about 72° F. (relative humidify varied between about 30 and about 99%) for 4 days. The plant were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table II.

EXAMPLE G

Bean Rust

The compound was evaluated for their ability to eradicate Bean Rust caused by *Uromyces phaseoli tipica* on pinto beans.

Pinto bean plants variety Idaho 1-11, 16 (summer) or 19 (winter) days old were inoculated with a 50 ppm suspension of uredospores in water containing a small amount of non-ionic surfactant. The inoculated plants were placed in an environmental chamber immediately after inoculation and incubated 20 hours. Following the incubation period, the plants were removed from the chamber and placed in a greenhouse maintained at 66°–68° F. and 60–80% relative humidity. Two days after inoculation, the plants were treated by spraying with a 200 ppm solution of test compound in an acetone and water carrier formulation containing a small amount of non-ionic surfactant. One or two replicate pots (each containing two plants) were used for each compound. In addition, one or two replicate pots were sprayed with the same carrier formulation (without a test compound) as a control (hereinafter "untreated checks"). The plants were kept in the greenhouse until evaluated. The plants were evaluated for disease control when disease symptoms were well developed on the untreated checks, normally about 14 days after treatment. The percentage disease control (or eradication) provided by a test compound was based on the percent disease reduction relative to the untreated checks. The results are reported in Table II.

EXAMPLE H

Rice Blast

The compound was tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X -77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated checks plants:

$$\% \text{ Control} = 100 - 100 \times \frac{(\% \text{ disease in treated plants})}{(\% \text{ disease in check})}$$

The results are tabulated in Table II.

TABLE I

Compounds of the Formula:

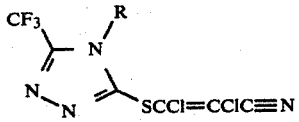

| | | | Elemental Analysis | | | | | |
|---|---|---|---|---|---|---|---|---|
| | | | % C | | % H | | % N | |
| Compound | R | Physical State | Calc. | Found | Calc. | Found | Calc. | Found |
| 1 38823 | —CH$_3$ | Light yellow solid, mp 90–94° C. | 27.73 | 29.97 | 1.00 | 1.26 | 18.48 | 21 |
| 2 42058 | —CH$_2$CH$_3$ | White solid, mp 69–71° C. | 30.3 | 30.6 | 1.60 | 1.52 | 17.7 | 17.7 |
| 3 42011 | —CH$_2$CH=CH$_2$ | Light yellow solid, mp 45–48° C. | 32.8 | 32.9 | 1.53 | 1.57 | 17.02 | 17.22 |

TABLE II

| | Mycelial Inhibition | | | | | | | | | | | |
|---|---|---|---|---|---|---|---|---|---|---|---|---|
| Compound | Pyth. | Rhiz. | Fusar. | Botr. | Asper. | GDM | TLB | CLB | TEB | BR | BPM | RB |
| 1 38823 | 62 | 171 | 73 | 62 | 23 | 98 | 71 | 46 | 69 | 4 | 0 | 0 |
| 2 42058 | 0 | 0 | 0 | 0 | 0 | 64 | 69 | 10 | — | 0 | 42 | 60 |
| 3 42011 | | | 59 | | | 97 | 21 | 67 | 0 | 0 | 0 | 27 |

Pyth. = *Pythium ultimum*
Rhiz. = *Rhizoctonia solari*
Fusar. = *Fusarium monilofroma*
Botr. = *Botrytis cinerea*
Asper. = *Aspergillus niger*
GDM = Grape Downy Mildew
TLB = Tomato Late Blight
CLB = Celery Late Blight
TEB = Tomato Early Blight
BR = Bean Rust Eradicant
BPM = Bean Powdery Mildew
RB = Rice Blast

What is claimed is:

1. A compound of the formula:

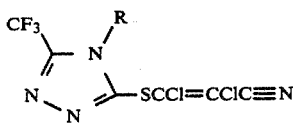

wherein R is lower alkyl or lower alkenyl.

2. A compound according to claim 1 wherein R is lower alkyl of 1 to 3 carbon atoms or allyl.
3. A compound according to claim 2 wherein R is methyl.
4. A compound according to claim 2 wherein R is allyl.
5. A method for controlling fungi which comprises contacting said fungi or their growth environment with a fungicidally effective amount of the compound of the formula defined in claim 1.
6. A method for controlling fungi which comprises contacting said fungi or their growth environment with a fungicidally effective amount of a compound of claim 3.
7. A method for controlling fungi which comprises contacting said fungi or their growth environment with a fungicidally effective amount of a compound of claim 3.
8. A method for controlling fungi which comprises contacting said fungi or their growth environment with a fungicidally effective amount of a compound of claim 4.
9. A fungicidal composition comprising an inert carrier and a fungicidally effective amount of a compound of claim 1.
10. A fungicidal composition comprising an inert carrier and a fungicidally effective amount of a compound of claim 2.
11. A fungicidal composition comprising an inert carrier and a fungicidally effective amount of a compound of claim 3.
12. A fungicidal composition comprising an inert carrier and a fungicidally effective amount of a compound of claim 4.

* * * * *